US011052141B1

(12) United States Patent
Henry et al.

(10) Patent No.: US 11,052,141 B1
(45) **Date of Patent: *Jul. 6, 2021**

(54) METHOD OF MODIFYING THE IMMUNE RESPONSE

(71) Applicant: KODE BIOTECH LIMITED, Auckland (NZ)

(72) Inventors: Stephen Micheal Henry, Auckland (NZ); Caroline Ann Oliver, Auckland (NZ)

(73) Assignee: KODE BIOTECH LIMITED, Auckland (NZ)

( * ) Notice: Subject to any disclaimer, the term of this patent is extended or adjusted under 35 U.S.C. 154(b) by 169 days.

This patent is subject to a terminal disclaimer.

(21) Appl. No.: 16/185,122

(22) Filed: Nov. 9, 2018

Related U.S. Application Data

(63) Continuation-in-part of application No. 14/794,850, filed on Jul. 9, 2015, now Pat. No. 10,124,047, which is a continuation of application No. 12/998,239, filed as application No. PCT/NZ2009/000209 on Oct. 2, 2009, now abandoned.

(30) Foreign Application Priority Data

| | | |
|---|---|---|
| Oct. 2, 2008 | (NZ) | 571727 |
| Jun. 12, 2009 | (NZ) | 577690 |

(51) Int. Cl.
*A61K 39/00* (2006.01)
*A61K 47/54* (2017.01)

(52) U.S. Cl.
CPC ........ *A61K 39/0013* (2013.01); *A61K 47/543* (2017.08); *A61K 2039/62* (2013.01)

(58) Field of Classification Search
None
See application file for complete search history.

(56) References Cited

U.S. PATENT DOCUMENTS

| | | | |
|---|---|---|---|
| 4,762,701 | A | 8/1988 | Horan et al. |
| 5,552,287 | A | 9/1996 | Kusakabe et al. |
| 2008/0312162 | A1 | 12/2008 | Sun et al. |

FOREIGN PATENT DOCUMENTS

| | | |
|---|---|---|
| WO | WO 2005/090368 | 9/2005 |
| WO | WO 2009/035347 | 3/2009 |

OTHER PUBLICATIONS

Bundle, D.R., et al; "Hybridomas Specific for Carbohydrates; Synthetic Human Blood Group Antigens for the Production, Selection, and Characterization of Monoclonal Typing Reagents"; *The Journal of Immunology*, vol. 129, No. 2; pp. 678-682 (1982).
Cairns, T.D.H., et al; "Xenografts—future prospects for clinical transplantation"; *Immunology Letters*, vol. 29, pp. 167-170 (1991).
Lang, K.S., et al; "Requirement for Neutralizing Antibodies to Control Bone Marrow Transplantation-Associated Persistent Viral Infection and to Reduce Immunopathology"; *The Journal of Immunology*, vol. 175, pp. 5524-5531 (2005).
Marcinkiewicz, J., et al; "Immunoregulatory mechanisms of action of intravenous gammaglobulin in Kawasaki syndrome"; *Przegla d lekarski*, vol. 55, No. 11 pp. 611-3, Ref.: 27 (1998) (Abstract).

*Primary Examiner* — Michail A Belyavskyi
(74) *Attorney, Agent, or Firm* — Nixon & Vanderhye P.C.

(57) ABSTRACT

Methods of mitigating the risk of rejection of an allograft or xenograft in an incompatible recipient by neutralizing one or more populations of circulating antibody cross-reactive with a carbohydrate antigen expressed by the allograft or xenograft. The method includes administering to the recipient by intravenous infusion a concentration of a synthetic antigen lipid construct sufficient to neutralize the one or more populations of circulating antibody in the recipient.

6 Claims, 2 Drawing Sheets

METHOD OF MODIFYING THE IMMUNE RESPONSE

This application is a Continuation-in-part of application Ser. No. 14/794,850 filed Jul. 9, 2015, which is a continuation of application Ser. No. 12/998,239 filed Jun. 13, 2011 (abandoned), which is the U.S. national phase of International Application No. PCT/NZ2009/000209 filed Oct. 2, 2009, which designated the U.S. and claims priority to NZ Application Nos. 577690 filed Jun. 12, 2009 and 571727 filed Oct. 2, 2008, the entire contents of each of which are hereby incorporated by reference.

TECHNICAL FIELD

The invention relates to a method of modifying the immune response in a mammal. In particular, the invention relates to a method of neutralizing circulating antibody.

BACKGROUND ART

The circulating antibodies of the ABO blood groups may trigger a hyperacute reaction where a recipient receives a transfusion of blood from an incompatible donor. Circulating antibodies against antigenic determinants (epitopes), including those of the ABO blood groups (glycotopes), are also a major impediment to achieving successful transplantation. Removing anti-A/B antibodies by plasma exchange or plasmapheresis, splenectomy, and use of anti-B cell immunosuppressants are widely adopted strategies to avoid antibody dependant rejection of ABO-incompatible allografts.

Both the hyperacute reactions and delayed vascular rejections arising from ABO-incompatible transfusions and transplantations are triggered by the binding of anti-A/B antibodies to the A/B glycotopes expressed on the transfused red blood cells (RBCs) or vascular endothelial cells of the transplanted allografts. The binding of anti-A/B antibodies activates complement, platelet aggregation, and inflammation, resulting in intravascular haemolysis or thrombosis and occlusion of blood flow leading to the possible death of the recipient.

A need clearly exists for a method of neutralizing circulating antibody, at least transiently, to assist in the treatment or prevention of hyperacute reactions and delayed vascular rejections arising from ABO-incompatible transfusions and transplantations. It is to be anticipated that if such a need can be met, that similar methods may be employed to treat or mitigate hyperacute reactions and delayed vascular rejections arising from other glycotope-incompatible transfusions and transplantations.

It is an object of the invention to provide a method of neutralizing circulating antibody. It is an object of the invention to provide a method to be used in mitigating the risk of a clinically significant reaction to an incompatible blood transfusion. It is an object of the invention to provide a method to be used in mitigating the risk of rejection by a subject of an incompatible allograft or xenograft. It is an object of the invention to provide a method to be used in treating a subject with a clinically significant reaction to an incompatible blood transfusion. These objects are to be read disjunctively with the object of to at least provide a useful choice.

DISCLOSURE OF INVENTION

In a first aspect the invention provides a method to be used in neutralizing one or more populations of circulating antibody in a subject mammal including the step of:

Administering to the subject mammal an amount of synthetic antigen-lipid construct (F-S-L);

where the antigen (F) is reactive with the one or more populations of circulating antibody.

Preferably, the administering to the subject mammal is by intravascular injection of a dispersion of the amount of synthetic antigen-lipid construct (F-S-L). More preferably, the administering to the subject mammal is by intravenous injection of a dispersion of the amount of synthetic antigen-lipid construct (F-S-L).

Preferably, the administering to the subject mammal is prior to transfusion or transplantation. More preferably, the administering to the subject mammal is prior to transfusion or transplantation of donor cells, tissues or organs expressing the antigen (F). Most preferably, the administering to the subject mammal is prior to transfusion or transplantation of donor cells, tissues or organs predetermined to express the antigen (F).

Preferably, the amount of synthetic antigen-lipid construct (F-S-L) is effective to neutralize the one or more populations of circulating antibody.

Preferably, the amount of synthetic antigen-lipid construct (F-S-L) is in the form of a formulation that excludes plasma.

Preferably, the method is to provide at least a transient tolerance of the transfusion or graft expressing the antigen in the subject mammal.

Preferably, the antigen-lipid construct (F-S-L) is of the structure:

$F\text{-}S_1\text{-}S_2\text{-}L$ where

F is the epitope of a carbohydrate antigen (glycotope);

$S_1$-$S_2$ is a spacer (S) linking F to L; and

L is a lipid selected from the group consisting of diacyl- and dialkyl-glycerolipids, including glycerophospholipids.

Preferably, F, $S_1$, $S_2$ and L are covalently linked.

Preferably, F is selected from the group consisting of: glycotopes of blood group antigens. More preferably, F is selected from the group consisting of: GalNAcα3(Fucα2)Galβ-; Galα3(Fucα2)Galβ-; GalNα3(Fucα2)Galβ-; Fucα2Galβ-; Galβ4GlcNAcβ3(Galβ4GlcNAcβ6)Galβ-; Galβ4GlcNAcβ3-; Galβ4Glcβ-; Galβ3GlcNAcβ-; Galβ3(Fucα4)GlcNAcβ-; Fucα2Galβ3(Fucα4)GlcNAcβ-; GalNAcα3(Fucα2)Galβ3(Fucα4)GlcNAcβ-; Galα3(Fucα2)Galβ3(Fucα4)GlcNAcβ-; Galβ4(Fucα3)GlcNAcβ-; Fucα2Galβ4(Fucα3)GlcNAcβ-; NeuAcα2-3)Galβ(Fucα4)GlcNAcβ-; NeuAcα2-3Galβ4(Fucα3)GlcNAcβ-; GalNAcβ4(NeuAcα2-3)Galβ4-; Galβ3GalNAcα-; NeuAcα2-3Galβ4-; NeuAcα2-6Galβ4-; Galα4Galβ4-; GalNAcβGalα4Galβ4-; Galα4Galβ4GlcNAcβ3-; Galβ3GalNAcβGalα4-; NeuAcα2-3Galβ3GalNAcβGalα4-; Galα3Galβ-; GalNAcα3GalNAcβGalα4-; and GalNAcβGalNAcβ3Galα4-. Most preferably, F is selected from the group consisting of: glycotopes of the ABO blood group antigens.

Preferably, $S_1$-$S_2$ is selected to provide an antigen-lipid construct that is dispersible in a biocompatible medium. More preferably, $S_1$-$S_2$ is selected to provide an antigen-lipid construct that is dispersible in water and preferentially partitions into the plasma relative to naturally occurring glycolipids.

Preferably, the antigen-lipid construct (F-S-L) is of the structure:

$F-S_1-S_2-L$ where

F is a mono-, di-, tri- or oligo-saccharide;

$S_1$ is 2-aminoethyl, 3-aminopropyl, 4-aminobutyl, or 5-aminopentyl;

$S_2$ is $—CO(CH_2)_2CO—$, $—CO(CH_2)_3CO—$, $—CO(CH_2)_4CO—$ or $—CO(CH_2)_5CO—$; and L is a diacyl- or dialkyl-glycerophospholipid.

Preferably, L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid. More preferably, the lipid is derived from one or more cis-desaturated fatty acids. Most preferably, L is selected from the group consisting of: 1,2-O-dioleoyl-sn-glycero-3-phosphatidylethanolamine (DOPE), 1,2-O-distearyl-sn-glycero-3-phosphatidylethanolamine (DSPE) and rac-1,2-dioleoylglycerol (DOG).

In preferred embodiments of the first aspect of the invention the antigen-lipid construct includes the substructure:

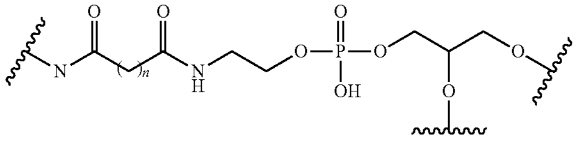

where n is the integer 2, 3, 4 or 5. More preferably, n is the integer 4.

In a first preferred embodiment of the first aspect of the invention the antigen-lipid construct (F-S-L) is the structure:

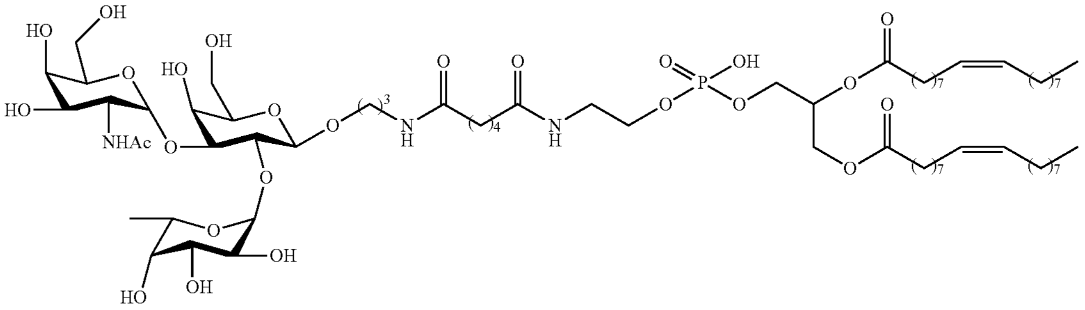

designated $A_{tri}$-$S_1$-$S_2$-DOPE.

In a second preferred embodiment of the first aspect of the invention the antigen-lipid construct (F-S-L) is the structure:

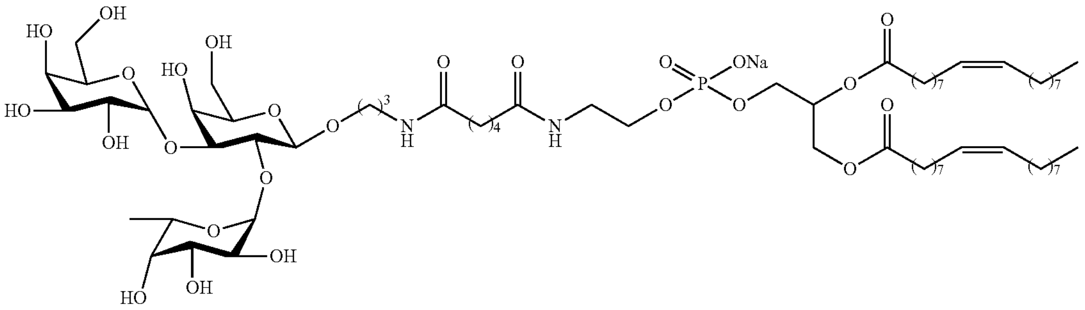

designated $B_{tri}$—$S_1$-$S_2$-DOPE.

In a third preferred embodiment of the first aspect of the invention the antigen-lipid construct (F-S-L) is the structure:

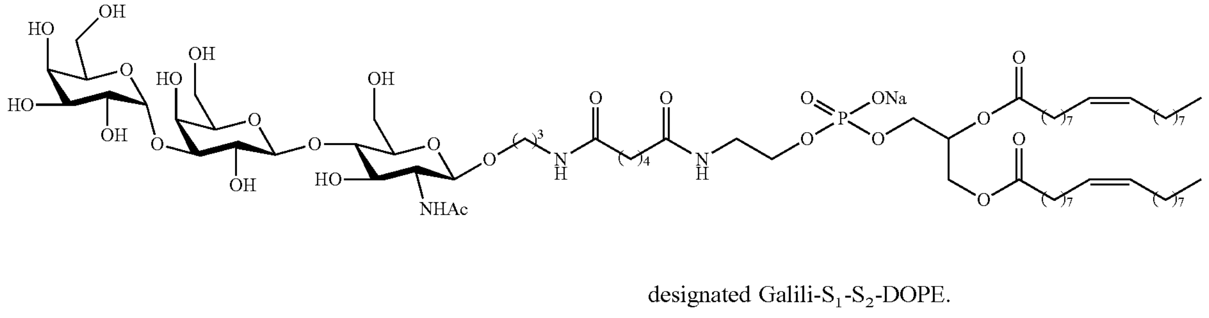

designated Galili-$S_1$-$S_2$-DOPE.

Preferably, the subject mammal is a human.

In a second aspect the invention provides a pharmaceutical preparation comprising a dispersion of synthetic antigen-lipid construct (F-S-L) for use in the method of the first aspect of the invention where the antigen-lipid construct is of the structure:

F—$S_1$—$S_2$-L and

F is the epitope of a carbohydrate antigen (glycotope);

$S_1$—$S_2$ is a spacer linking F to L; and

L is a lipid selected from the group consisting of diacyl- and dialkyl-glycerolipids, including glycerophospholipids.

Preferably, F, $S_1$, $S_2$ and L are covalently linked.

Preferably, the dispersion of synthetic antigen-lipid construct (F-S-L) is at a concentration of at least 10 μmol. More preferably, the dispersion of synthetic antigen-lipid construct (F-S-L) is at a concentration of at least 15 μmol. Most preferably, the dispersion of synthetic antigen-lipid construct (F-S-L) is at a concentration of at least 17.5 μmol.

Preferably, the dispersion of synthetic antigen-lipid construct (F-S-L) is a dispersion in human red cell transfusion medium.

In a third aspect the invention provides the use of an amount of synthetic antigen-lipid construct (F-S-L) in the manufacture of a preparation for neutralizing one or more populations of circulating antibody in a subject mammal.

In a first preferred embodiment the preparation is a medicament for administration to a human prior to transfusion to mitigate the risk of a clinically significant reaction to a donor antigen.

In a second preferred embodiment the preparation is a medicament for administration to a human prior to transplantation to mitigate the risk of a clinically significant reaction to a donor antigen.

Preferably, the antigen-lipid construct (F-S-L) is of the structure:

F-$S_1$-$S_2$-L where

F is the epitope of a carbohydrate antigen (glycotope);

$S_1$-$S_2$ is a spacer linking F to L; and

L is a lipid selected from the group consisting of diacyl- and dialkyl-glycerolipids, including glycerophospholipids.

Preferably, F is selected from the group consisting of: glycotopes of blood group antigens. More preferably, F is selected from the group consisting of: GalNAcα3(Fucα2)Galβ-; Galα3(Fucα2)Galβ-; GalNα3(Fucα2)Galβ-; Fucα2Galβ-; Galβ4GlcNAcβ3(Galβ4GlcNAcβ6)Galβ-; Galβ4GlcNAcβ3-; Galβ4Glcβ-; Galβ3GlcNAcβ-; Galβ3(Fucα4)GlcNAcβ-; Fucα2Galβ3(Fucα4)GlcNAcβ-; GalNAcα3(Fucα2)Galβ3(Fucα4)GlcNAcβ-; Galα3(Fucα2)Galβ3(Fucα4)GlcNAcβ-; Galβ4(Fucα3)GlcNAcβ-; Fucα2Galβ4(Fucα3)GlcNAcβ-; NeuAcα2-3Galβ3(Fucα4)GlcNAcβ-; NeuAcα2-3Galβ4(Fucα3)GlcNAcβ-; GalNAcβ4(NeuAcα2-3)Galβ4-; Galβ3GalNAcα-; NeuAcα2-3Galβ4-; NeuAcα2-6Galβ4-; Galα4Galβ4-; GalNAcβGalα4Galβ4-; Galα4Galβ4GlcNAcβ3-; Galβ3GalNAcβGalα4-; NeuAcα2-3Galβ3GalNAcβGalα4-; Galα3Galβ-; GalNAcα3GalNAcβGalα4-; and GalNAcβGalNAcβGalα4-. Most preferably, F is selected from the group consisting of: glycotopes of the ABO blood group antigens and Galili antigen.

Preferably, $S_1$-$S_2$ is selected to provide an antigen-lipid construct that is dispersible in a biocompatible medium. More preferably, $S_1$—$S_2$ is selected to provide an antigen-lipid construct that is dispersible in water and preferentially partitions into the plasma relative to naturally occurring glycolipids.

Preferably, L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid. More preferably, the lipid is derived from one or more cis-desaturated fatty acids. Most preferably, L is selected from the group consisting of: 1,2-O-dioleoyl-sn-glycero-3-phosphatidylethanolamine (DOPE), 1,2-O-distearyl-sn-glycero-3-phosphatidylethanolamine (DSPE) and rac-1,2-dioleoylglycerol (DOG).

In the preferred embodiments of the third aspect of the invention the antigen-lipid construct (F-S-L) preferably includes the substructure:

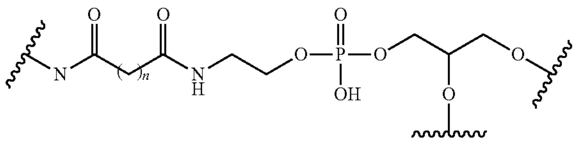

where n is the integer 2, 3, 4 or 5. More preferably, n is the integer 4.

In the preferred embodiments of the third aspect of the invention the antigen-lipid construct (F-S-L) is preferably of the structure:

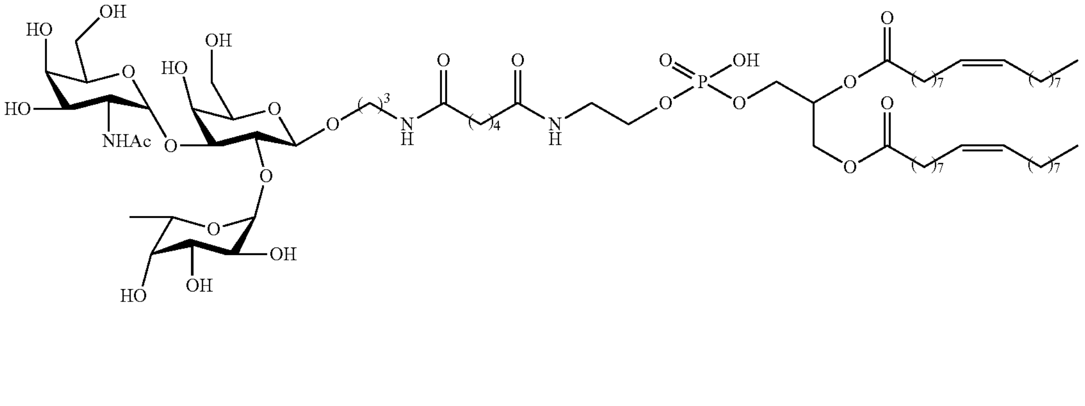

designated $A_{tri}$-$S_1$-$S_2$-DOPE,

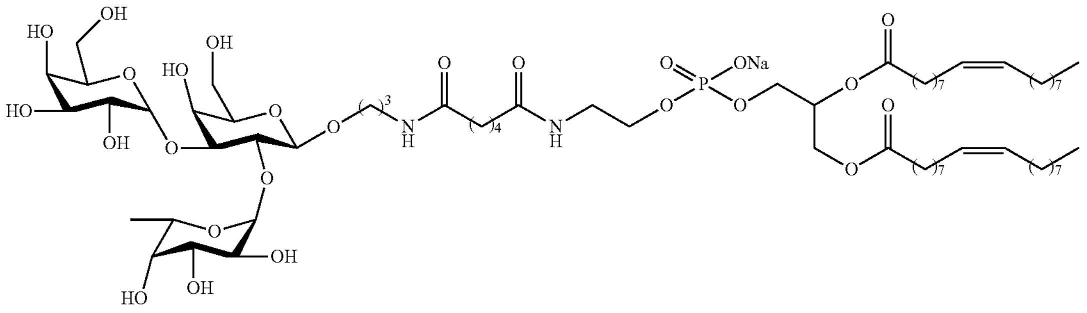

designated $B_{tri}$—$S_1$-$S_2$-DOPE, or

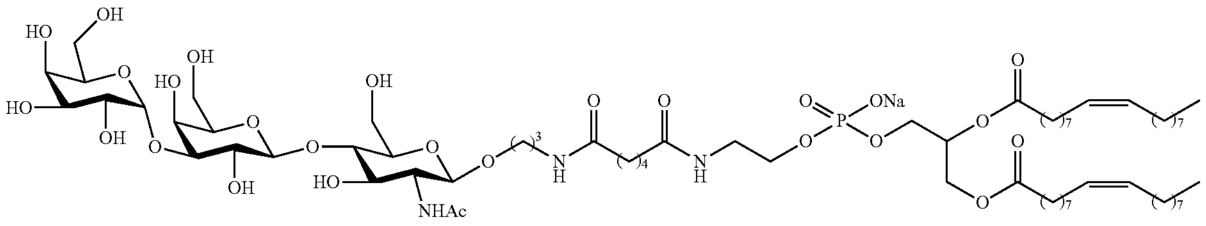

designated Galili-$S_1$-$S_2$-DOPE.

In a fourth aspect the invention provides a method of modifying the profile of circulating antibody in the plasma of a subject mammal comprising the step of:

Administering to the subject mammal an amount of synthetic antigen-lipid construct of the structure F—$S_1$—$S_2$-L;

where

F is the epitope of a carbohydrate antigen (glycotope) reactive with one or more populations of the circulating antibody;

$S_1$-$S_2$ is a spacer linking F to L; and

L is a lipid selected from the group consisting of diacyl- and dialkyl-glycerolipids, including glycerophospholipids.

Preferably, the administering to the subject mammal is by intravascular injection of a dispersion of the amount of synthetic antigen-lipid construct. More preferably, the administering to the subject mammal is by intravenous injection of a dispersion of the amount of synthetic antigen-lipid construct.

Preferably, F is selected from the group consisting of: glycotopes of blood group antigens. More preferably, F is selected from the group consisting of: GalNAcα3(Fucα2)Galβ-; Galα3(Fucα2)Galβ-; GalNα3(Fucα2)Galβ-; Fucα2Galβ-; Galβ4GlcNAcβ3(Galβ4GlcNAcβ6)Galβ-; Galβ4GlcNAcβ3-; Galβ4Glcβ-; Galβ3GlcNAcβ-; Galβ3(Fucα4)GlcNAcβ-; Fucα2Galβ3(Fucα4)GlcNAcβ-; GalNAcα3(Fucα2)Galβ3(Fucα4)GlcNAcβ-; Galα3(Fucα2)Galβ3(Fucα4)GlcNAcβ-; Galβ4(Fucα3)GlcNAcβ-; Fucα2Galβ4(Fucα3)GlcNAcβ-; NeuAcα2-3Galβ3(Fucα4)GlcNAcβ-; NeuAcα2-3Galβ4(Fucα3)GlcNAcβ-; GalNAcβ4(NeuAcα2-3)Galβ4-; Galβ3GalNAcα-; NeuAcα2-3Galβ4-; NeuAcα2-6Galβ4-; Galα4Galβ4-; GalNAcβGalα4Galβ4-; Galα4Galβ4GlcNAcβ3-; Galβ3GalNAcβGalα4-; NeuAcα2-3Galβ3GalNAcβGalα4-; Galα3Galβ-; GalNAcα3GalNAcβGalα4-; and GalNAcβGalNAcβGalα4-. Most preferably, F is selected from the group consisting of: glycotopes of the ABO blood group antigens.

Preferably, $S_1$—$S_2$ is selected to provide an antigen-lipid construct that is dispersible in a biocompatible medium. More preferably, $S_1$—$S_2$ is selected to provide an antigen-lipid construct that is dispersible in water and preferentially partitions into the plasma relative to naturally occurring glycolipids.

Preferably, L is selected from the group consisting of: diacylglycerolipids, phosphatidate, phosphatidyl choline, phosphatidyl ethanolamine, phosphatidyl serine, phosphatidyl inositol, phosphatidyl glycerol, and diphosphatidyl glycerol derived from one or more of trans-3-hexadecenoic acid, cis-5-hexadecenoic acid, cis-7-hexadecenoic acid, cis-9-hexadecenoic acid, cis-6-octadecenoic acid, cis-9-octadecenoic acid, trans-9-octadecenoic acid, trans-11-octadecenoic acid, cis-11-octadecenoic acid, cis-11-eicosenoic acid or cis-13-docsenoic acid. More preferably, the lipid is derived from one or more cis-desaturated fatty acids. Most preferably, L is selected from the group consisting of: 1,2-O-dioleoyl-sn-glycero-3-phosphatidylethanolamine (DOPE), 1,2-O-distearyl-sn-glycero-3-phosphatidylethanolamine (DSPE) and rac-1,2-dioleoylglycerol (DOG).

In preferred embodiments of the fourth aspect of the invention the antigen-lipid construct (F-S-L) includes the substructure:

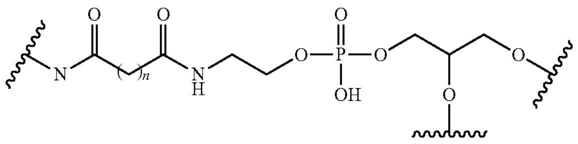

where n is the integer 2, 3, 4 or 5. More preferably, n is the integer 4.

In a first preferred embodiment of the fourth aspect of the invention the antigen-lipid construct (F-S-L) is the structure:

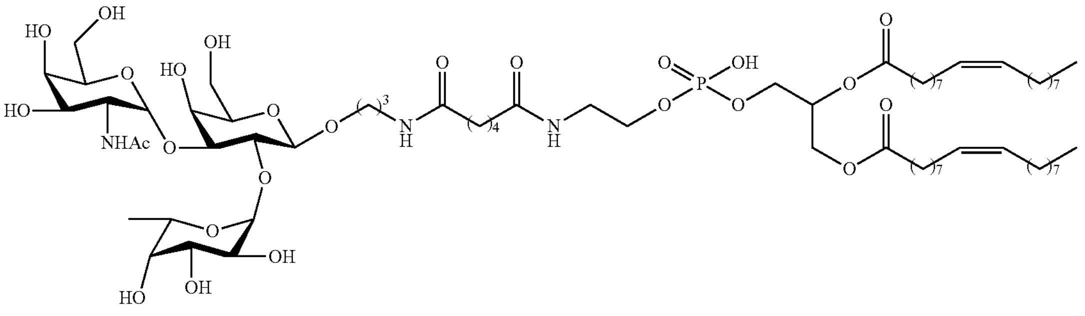

designated $A_{tri}$-$S_1$-$S_2$-DOPE.

In a second preferred embodiment of the fourth aspect of the invention the antigen-lipid construct (F-S-L) is the structure:

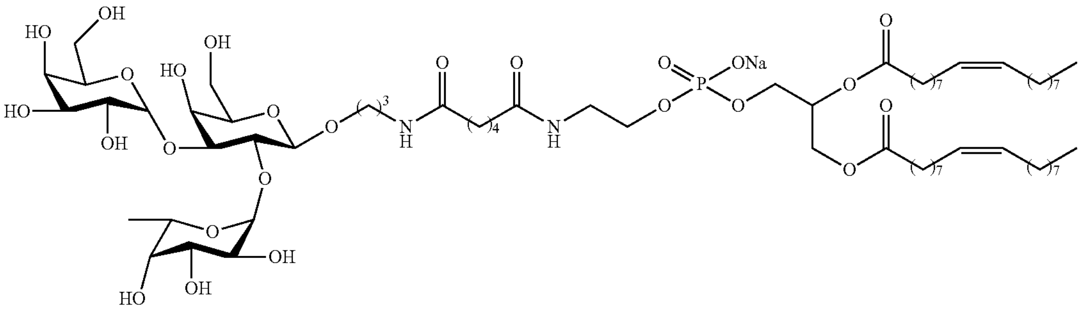

designated $B_{tri}$—$S_1$-$S_2$-DOPE.

In a third preferred embodiment of the fourth aspect of the invention the antigen-lipid construct (F-S-L) is the structure:

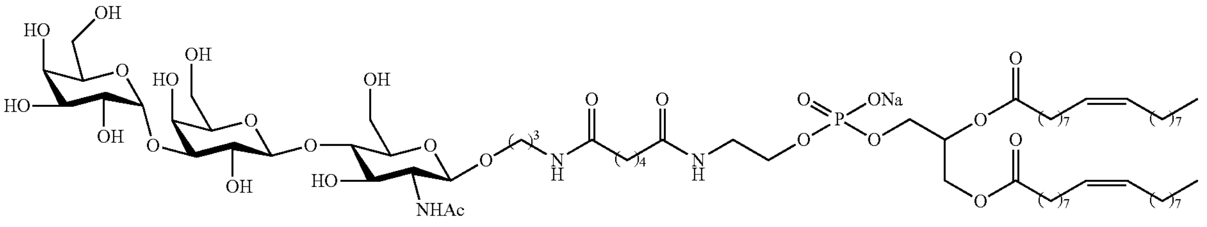

designated Galili-$S_1$-$S_2$-DOPE.

In the description and claims of this specification the following acronyms, terms and phrases are intended to have the meaning indicated: “Clinically significant” means an adverse event that requires intervention by a clinician or hospitalization. “Dispersible” means a stable, single phase system is formed when the antigen-lipid construct is contacted with an aqueous vehicle such as serum or plasma in the absence of organic solvents or detergents, and the term “dispersion” has a corresponding meaning. “Donor” means the subject from which the cells, tissues or organs are obtained. “Glycotope” means the epitope of a carbohydrate antigen. “Incompatible” means:

in reference to an antigen, an antigen for which a clinically significant humoral and/or cell mediated specific immune response occurs or is occurring; and in reference to a blood transfusion, a blood transfusion where the plasma of the recipient contains antibodies to an antigen of the donor at a sufficiently high titre to cause a clinically significant humoral and/or cell mediated specific immune response.

“Intravascular” means delivery into the vascular fluids (blood, lymph) of the body, and includes intravenous delivery. “Neutralise” means that the recipient does not experience a clinically significant response following the transfusion of blood or transplantation of cells expressing antigen for which the recipient expresses antibody, and the term “neutralising” has a corresponding meaning. “pcv” denotes packed cell volume. “Plasma” means the colourless fluid part of blood or lymph, in which corpuscles or fat globules are suspended. “hRBC” denotes human red blood cells. “mRBC” denotes mouse red blood cells. “rRBC” denotes rabbit red blood cells. “Saline” means a solution of one or more salts. “Serum” means the amber-coloured, protein-rich liquid which separates out when blood coagulates. “Synthetic” means made by chemical synthesis.

The term “antigen” is to be understood in a functional sense, i.e. structures capable of eliciting an antibody mediated immune response.

In the representations of the structures or substructures of compounds the repeat of a divalent radical is represented by:

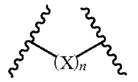

where —X— is the divalent radical repeated n times. Where the divalent radical is methylene (—$CH_2$—) the repeat of this divalent radical is represented by:

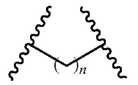

The invention will now be described with reference to embodiments or examples and the figures of the accompanying drawings pages.

DETAILED DESCRIPTION

Figure 1:
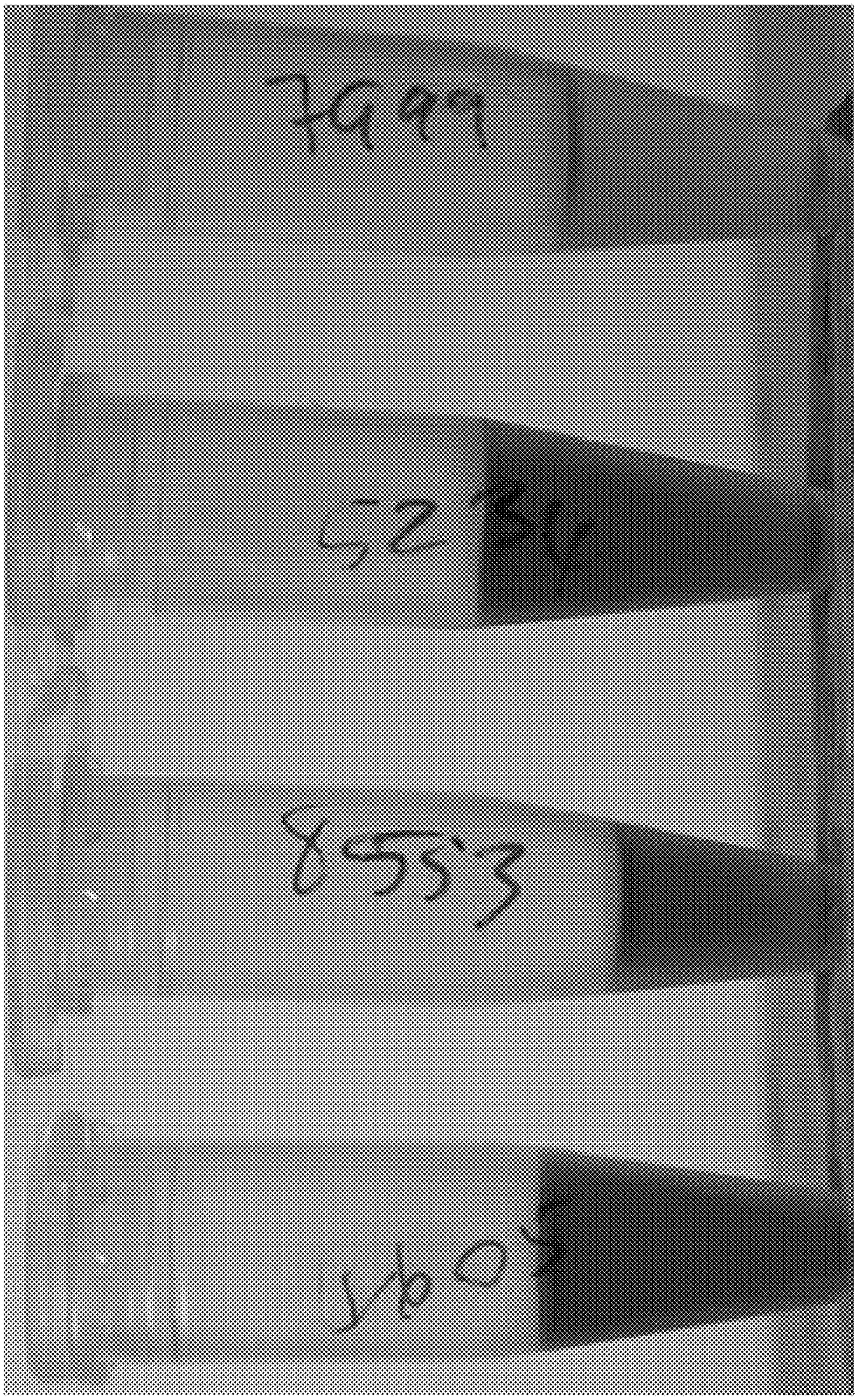
FIG. 1. Urine samples (30 minutes post infusion with murine A kodecytes): L to R—ID #4605, ID #8553, ID #5234, ID #7999 (control).

The antigen-lipid constructs of the invention are administered by intravascular injection. It is a requirement of this mode of administration that the antigen-lipid constructs are delivered in a biocompatible medium. Antigen-lipid constructs that are dispersible in biocompatible media at a concentration sufficient to allow administration at a rate sufficient to neutralise one or more populations of circulating antibody or induce at least a transient tolerance of the antigen are required. It is a particular advantage of the synthetic antigen-lipid constructs of the invention that there is no significant activation of the complement cascade.

Antigen-lipid constructs with these required properties are prepared by covalently joining the epitope of the carbohydrate antigen (glycotope) to a diacyl or dialkyl lipid via a spacer. The spacer is selected to impart the required dispersibility on the antigen-lipid construct. When administered into the vascular system the antigen-lipid construct is anticipated to partition between the plasma and membranes of the cells of the circulatory and lymphatic systems (red blood cells (RBCs), lymphocytes), but with a greater propensity to partition into the plasma than a naturally occurring glycolipid (glycosphingolipid) counterpart. Whilst not wishing to be bound by theory it is anticipated that it is this ability of the antigen-lipid constructs to partition between both the plasma and membranes of cells of the vascular system that provides for the observed neutralization of circulating antibody.

In one application it is proposed that the antigen-lipid constructs are administered by intravenous injection or infusion to mitigate the risk of a hemolytic response arising from the presence of reactive circulating antibody in an incompatible recipient of transfused blood. Reactive circulating antibody to one or more of the following antigens may be present in a recipient:

| Antigen | Glycotope |
|---|---|
| A | GalNAcα3(Fucα2)Galβ-R |
| B | Galα3(Fucα2)Galβ-R |
| Acquired B | GalNα3(Fucα2)Galβ-R |
| H | Fucα2Galβ-R |
| I | Galβ4GlcNAcβ3(Galβ4GlcNAcβ6)Galβ-R |
| i | Galβ4GlcNAcβ3-R |
| Lactosyl | Galβ4Glcβ-R |
| Lec | Galβ3GlcNAcβ-R |
| Lea | Galβ3(Fucα4)GlcNAcβ-R |
| Leb | Fucα2Galβ3(Fucα4)GlcNAcβ-R |
| ALeb | GalNAcα3(Fucα2)Galβ3(Fucα4)GlcNAcβ-R |
| BLeb | Galα3(Fucα2)Galβ3(Fucα4)GlcNAcβ-R |
| X | Galβ4(Fucα3)GlcNAcβ-R |
| Y | Fucα2Galβ4(Fucα3)GlcNAcβ-R |
| Sialyl Lea | NeuAcα2-3Galβ3(Fucα4)GlcNAcβ-R |
| Sialyl Lex | NeuAcα2-3Galβ4(Fucα3)GlcNAcβ-R |
| Cad | GalNAcβ4(NeuAcα2-3)Galβ4-R |
| T | Galβ3GalNAcα-R |
| Sialyl | NeuAcα2-3Galβ4-R |
| Sialyl | NeuAcα2-6Galβ4-R |
| Pk | Galα4Galβ4-R |
| P | GalNAcβ3Galα4Galβ4-R |
| P1 | Galα4Galβ4GlcNAcβ3-R |
| SSEA-3 | Galβ3GalNAcβ3Galα4-R |
| LKE | NeuAcα2-3Galβ3GalNAcβ3Galα4-R |
| Galili | Galα3Galβ-R |
| Forssman | GalNAcα3GalNAcβ3Galα4-R |
| paraForssman | GalNAcβ3GalNAcβ3Galα4-R |

It is contemplated that antigen-lipid constructs (F-S-L) where F is one of the foregoing glycotopes may be prepared and used in the methods of the invention. The antigen-lipid constructs (F-S-L) would be of the following generalized structures:

GalNAcα3(Fucα2)Galβ-$S_1$-$S_2$-L
Galα3(Fucα2)Galβ-$S_1$-$S_2$-L
GalNAcα3(Fucα2)Galβ-$S_1$-$S_2$-L
Fucα2Galβ-$S_1$-$S_2$-L
Galβ4GlcNAcβ3(Galβ4GlcNAcβ6)Galβ-$S_1$-$S_2$-L
Galβ4GlcNAcβ3-$S_1$-$S_2$-L
Galβ4Glcβ-$S_1$-$S_2$-L
Galβ3GlcNAcβ-$S_1$-$S_2$-L
Galβ3(Fucα4)GlcNAcβ-$S_1$-$S_2$-L
Fucα2Galβ3(Fucα4)GlcNAcβ-$S_1$-$S_2$-L
GalNAcα3(Fucα2)Galβ3(Fucα4)GlcNAcβ-$S_1$-$S_2$-L
Galα3(Fucα2)Galβ3(Fucα4)GlcNAcβ-$S_1$-$S_2$-L
Galβ4(Fucα3)GlcNAcβ-$S_1$-$S_2$-L
Fucα2Galβ4(Fucα3)GlcNAcβ-$S_1$-$S_2$-L
NeuAcα2-3Galβ3(Fucα4)GlcNAcβ-$S_1$-$S_2$-L
NeuAcα2-3Galβ4(Fucα3)GlcNAcβ-$S_1$-$S_2$-L
GalNAcβ4(NeuAcα2-3)Galβ4-$S_1$-$S_2$-L
Galβ3GalNAcα-$S_1$-$S_2$-L
NeuAcα2-3Galβ4-$S_1$-$S_2$-L
NeuAcα2-6Galβ4-$S_1$-$S_2$-L
Galα4Galβ4-$S_1$-$S_2$-L
GalNAcβGalα4Galβ4-$S_1$-$S_2$-L
Galα4Galβ4GlcNAcβ3-$S_1$-$S_2$-L
Galβ3GalNAcβGalα4-$S_1$-$S_2$-L
NeuAcα2-3Galβ3GalNAcβGalα4-$S_1$—$S_2$-L
Galα3Galβ-$S_1$—$S_2$-L
GalNAcα3GalNAcβGalα4-$S_1$—$S_2$-L
GalNAcβ3GalNAcβGalα4-$S_1$—$S_2$-L where $S_1$—$S_2$-L are as defined under the heading Disclosure of Invention.

A phenomenon documented in transfusion medicine is the ability of Lewis glycolipids present in plasma to temporarily neutralise circulating antibodies (Mollison et al (1972)). Lewis antibodies are potent haemolytic antibodies which can result in severe haemolytic transfusion reactions. Individuals who have no option other than to undergo a transfusion with Lewis (blood group antigen) incompatible blood are firstly infused with 1 unit of Lewis positive plasma. This neutralises the circulating antibody and is immediately followed by the transfusion of incompatible red blood cells. The extent to which the administered antigen-lipid construct incorporates non-specifically in to the outer membranes of cells will depend in part on the amount administered and the dosage form, e.g. a pharmaceutically acceptable preparation that is a dispersion, or a pharmaceutically acceptable preparation that is a suspension of liposomes.

A pilot study in rabbits demonstrated it was possible to drastically reduce the antibody titre of one animal from 1:512 to 1:8 after one infusion of 20 mg of antigen-lipid construct 4 hours post infusion. In another animal, the antibody titre dropped from 1:256 to 1:2 after one infusion of 36 mg of antigen-lipid construct 24 hours post infusion. Furthermore, in a third animal, the subject mammal's antibody titre was still significantly reduced from 1:32 to 1:8, 5 days after one infusion of 30 mg of antigen-lipid construct. Further studies were subsequently performed to confirm circulating antibody in subject mammals can be neutralised by intravenous injection of synthetic antigen-lipid constructs. The sustainability of neutralization over a short period of time was also assessed.

Without inferring any limitation on the general applicability of the proposed method of neutralizing one or more populations of circulating antibody, a synthetic antigen-lipid construct of the following structure:

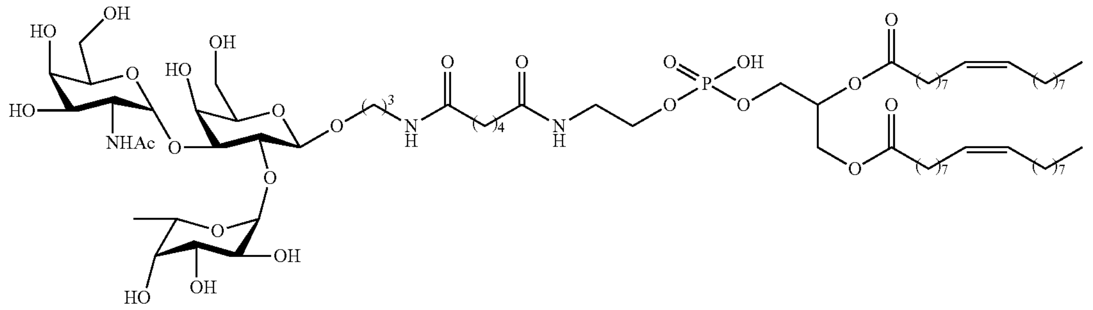

and designated $A_{tri}$-$S_1$—$S_2$-DOPE was used. It will be recognized that synthetic antigen-lipid constructs including different epitopes may be used alone or in combination in the proposed method to neutralize one or more populations of reactive circulating antibody.

Experimental Procedures

Preparation of Constructs

The Preparation of Synthetic Antigen-Lipid Constructs where the Epitope of the antigen-lipid construct is a carbohydrate (glycotope) such as $A_{tri}$ or $B_{tri}$ is described in the specification accompanying international application no. PCT/NZ2005/000052 (publication no. WO 2005/090368). The preparation of synthetic antigen-lipid constructs where the epitope of the antigen-lipid construct is a carbohydrate (glycotope) such as Galili is described in the specification accompanying international application no. PCT/GB2015/051368 (publication no. WO 2015/170121 A1). For the sake of completeness a detailed description of the preparation and characterization of the construct designated Galili-$S_1$-$S_2$-DOPE is provided.

Materials and Methods

Thin layer chromatography (TLC) was performed on silica gel 60 $F_{254}$ plates (Merck). Compounds were visualised by applying 8% (w/v) phosphoric acid in water followed by heating at over 150° C.

Column chromatography (CC) was performed on silica gel 60 (0.063 to 0.200 mm (70 to 230 mesh ASTM)) (Merck)(CAS RN 7631-86-9), SEPHADEX™ LH-20 (GE Healthcare) (CAS RN 9041-37-6) or protonated ($H^+$) DOWEX™ 50×4-400 (CAS RN 69011-20-7) (Sigma).

Proton ($^1H$) nuclear magnetic resonance (NMR) spectra were acquired on a Bruker DRX 500 or BioSpin GmbH (700 MHz) instrument at 30° C. Chemical shifts are provided in ppm (δ) relative to deuterated water ($D_2O$), chloroform ($CDCl_3$) or methanol ($CD_3OD$). Coupling constants (J) were measured in Hz. Symbols of monosaccharide residues in NMR spectra for saccharides: I (β-GlcNAc; reducing end), II (β-Gal) and III (α-Gal).

MALDI TOF MS spectra were recorded on Bruker Daltonics Ultraflex MALDI TOF/TOF Mass Spectrometer (Germany).

Preparation of the 2,5-dioxo-1-pyrrolidinyl ester of (25Z)-11-oxide-11-hydroxy-6,17-dioxo-14-[[(9Z)-1-oxo-9-octadecen-1-yl]oxy]-10,12,16-trioxa-7-aza-11-phosphatetratriacont-25-enoic acid ("activated lipid"; A-L) (CAS RN 9300280-91-4) (3)

To a solution of bis(N-hydroxysuccinimidyl) adipate (1) (70 mg, 205 μmol) in dry N,N-dimethylformamide (1.5 mL) were added 1,2-dioleoyl-sn-glycero-3-phosphatidylethanolamine (2) (CAS RN 4004-05-1) (40 μmol) in chloroform (1.5 mL) followed by triethylamine (7 μL). The mixture was maintained for 2 hours at room temperature, then neutralized with acetic acid and partially concentrated in vacuo.

Column chromatography (1:1(v/v) chloroform-methanol, 0.2% (w/v) acetic acid) of the residue yielded the activated lipid (A-L) (3)(37 mg, 95%) as a colourless syrup. Thin layer chromatography (6:3:0.5 (v/v/v) chloroform-methanol-water) of the activated lipid (3) provided a retardation factor ($R_f$) of 0.5. $^1H$ NMR (2:1 (v/v) $CDCl_3/CD_3OD$) δ: 5.5 (m, 4H, 2x(—$\underline{H}$C═C$\underline{H}$—), 5.39 (m, 1H, —$OCH_2$—C$\underline{H}$O—$CH_2O$—), 4.58 (dd, 1H, J=3.67, J=11.98, —CCOOHC$\underline{H}$—CHO—$CH_2O$—), 4.34 (dd, 1H, J=6.61, J=11.98, —CCOO$\underline{H}$CH—CHO—$CH_2O$—), 4.26 (m, 2H, PO-C$\underline{H}_2$—$CH_2$—$NH_2$), 4.18 (m, 2H, —C$\underline{H}_2$—OP), 3,62 (m, 2H, PO—$CH_2$—C$\underline{H}_2$—$NH_2$), 3.00 (s, 4H, ONSuc), 2.8 (m, 2H, —C$\underline{H}_2$—CO (Ad), 2.50 (m, 4H, 2x(—C$\underline{H}_2$—CO), 2.42 (m, 2H, —C$\underline{H}_2$—CO (Ad), 2.17 (m, 8H, 2x(—C$\underline{H}_2$—CH═CH—C$\underline{H}_2$—), 1.93 (m, 4H, $COCH_2CH_2$C$\underline{H}_2$C$\underline{H}_2$CO), 1.78 (m, 4H, 2x($COCH_2$C$\underline{H}_2$—), 1,43, 1.47 (2 bs, 40H, 20 $CH_2$), 1.04 (m, 6H, 2 $CH_3$).

SCHEME I

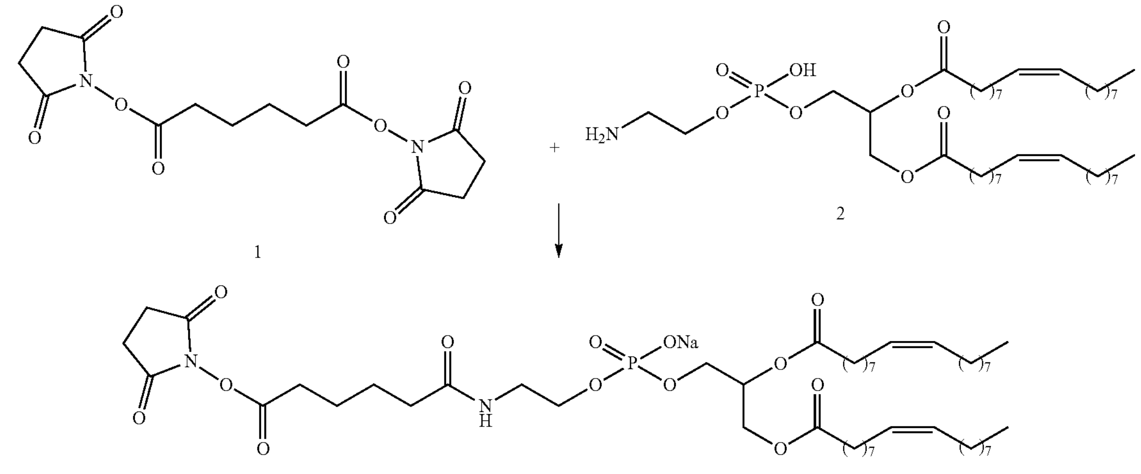

1 2 3

Preparation of 3-trifluoroacetamidopropyl-3,4-di-O-acetyl-2,6-di-O-benzyl-α-D-galactopyranosyl-(1→3)-2,4-di-O-acetyl-6-O-benzyl-β-D-galactopyranosyl-(1→4)-2-acetamido-3-O-acetyl-6-O-benzyl-2-deoxy-β-D-glucopyranoside (6)

The glycosyl acceptor (3-trifluoroacetamidopropyl)-2-acetamido-3-O-acetyl-6-O-benzyl-2-deoxy-4-O-(2,4-di-O-acetyl-6-O-benzyl-(3-D-galactopyranosyl)-β-D-glucopyranoside (5) was prepared according to the method disclosed in the publication of Pazynina et al (2008). A mixture of the glycosyl acceptor 5 (500 mg, 0.59 mmol), thiogalactopyranoside 4 (576 mg, 1.18 mmol), NIS (267 mg, 1.18 mmol), anhydrous $CH_2Cl_2$ (25 ml) and molecular sieves 4 Å (500 mg) was stirred at −45° C. for 30 min under an atmosphere of Ar. A solution of TfOH (21 μl, 0.236 mmol) in anhydrous $CH_2Cl_2$ (0.5 ml) was then added. The reaction mixture was stirred for 2 h at −45° C. and the temperature was then increased to −20° C. over 4 h. The mixture was kept at −20° C. overnight. Then extra amounts of thiogalactopyranoside 4 (144 mg, 0.295 mmol), NIS (66 mg, 0.295 mmol) and TfOH (5 μl, 0.06 mmol) were added and the stirring maintained at −20° C. for 2 h before being allowed to slowly warm up to r.t. (1 h). A saturated aqueous solution of $Na_2S_2O_3$ was then added and the mixture filtered. The filtrate was diluted with $CHCl_3$ (300 ml), washed with $H_2O$ (2×100 ml), dried by filtration through cotton wool, and concentrated. Gel filtration on LH-20 ($CHCl_3$-MeOH) afforded the product 6 (600 mg, 80%), as a white foam.

$^1H$ NMR (700 MHz, $CDCl_3$, characteristic signals), δ, ppm: 1.78-1.82 (m, 4H, CHCHC, $OC(O)CH_3$), 1.84-1.90 (m, 1H, CHCHC), 1.91, 1.94, 1.97, 1.98, 2.06 (5 s, 5×3H, 4 $OC(O)CH_3$, $NH(O)CH_3$), 3.23-3.30(m, 1H, NCHH), 3.59-3.65 (m, 1H, NCHH), 4.05 (m, 1H, H-$2^{I}$), 4.33 (d, 1H, $J_{1,2}$ 7.55, H-$1^{I}$), 4.40 (d, 1H, J 12.04, PhCHH), 4.42 (d, 1H, $J_{1,2}$ 8.07, H-$1^{II}$), 4.45 (d, 1H, J 11.92, PhCHH), 4.48 (d, 1H, J 12.00, PhCHH), 4.50 (d, 1H, J 12.00, PhCHH), 4.52 (d, 1H, J 12.04, PhCHH), 4.54 (d, 1H, J 12.00, PhCHH), 4.57 (d, 1H, J 12.00, PhCHH), 4.64(d, 1H, J 11.92, PhCHH), 4.99 (dd≈t, 1H, J 8.24, H-$2^{II}$), 5.08-5.13 (m, 2H, H-$3^{I}$, H-$3^{III}$), 5.23 (d, 1H, $J_{1,2}$ 3.31, H-$1^{III}$), 5.46 (d, 1H, $J_{3,4}$ 2.25, H-$4^{II}$), 5.54 (d, 1H, $J_{3,4}$ 3.11, H-$4^{III}$), 7.20-7.40 (m, 20H, ArH); 7.49-7.54 (m, 1H, $NHC(O)CF_3$). $R_f$ 0.4 ($PhCH_3$—AcOEt, 1:2).

Preparation of 3-aminopropyl-α-D-galactopyranosyl-(1→3)-β-D-galactopyranosyl-(1→4)-2-acetamido-2-deoxy-β-D-glucopyranoside ("Galili-$S_1$"; Galα3Galβ4GlcNAc-$S_I$) (CAS RN 215314-98-0) (8)

The product 6 (252 mg, 0.198 mmol) was deacetylated according to Zemplen (8 h, 40° C.), neutralized with AcOH and concentrated. The TLC ($CH_3Cl$-MeOH, 10:1) analysis of the obtained product showed two spots: the main spot with $R_f$ 0.45, and another one on the start line (ninhydrin positive spot) that was an indication of partial loss of trifluoroacetyl. Therefore, the product was N-trifluoroacetylated by treatment with $CF_3COOMe$ (0.1 ml) and $Et_3N$ (0.01 ml) in MeOH (10 ml) for 1 h, concentrated and subjected to column chromatography on silica gel ($CHCl_3$-MeOH, 15:1) to afford the product 7 as a white foam (163 mg, 77%), $R_f$ 0.45 ($CH_3Cl$-MeOH, 10:1). The product 7 was subjected to hydrogenolysis (200 mg Pd/C, 10 ml MeOH, 2 h), filtered, N-defluoroacetylated (5% $Et_3N/H_2O$, 3 h) and concentrated. Cation-exchange chromatography on Dowex 50×4-400 ($H^+$) (elution with 5% aqueous ammonia) gave the product 8 (90 mg, 98%) as a white foam.

SCHEME II

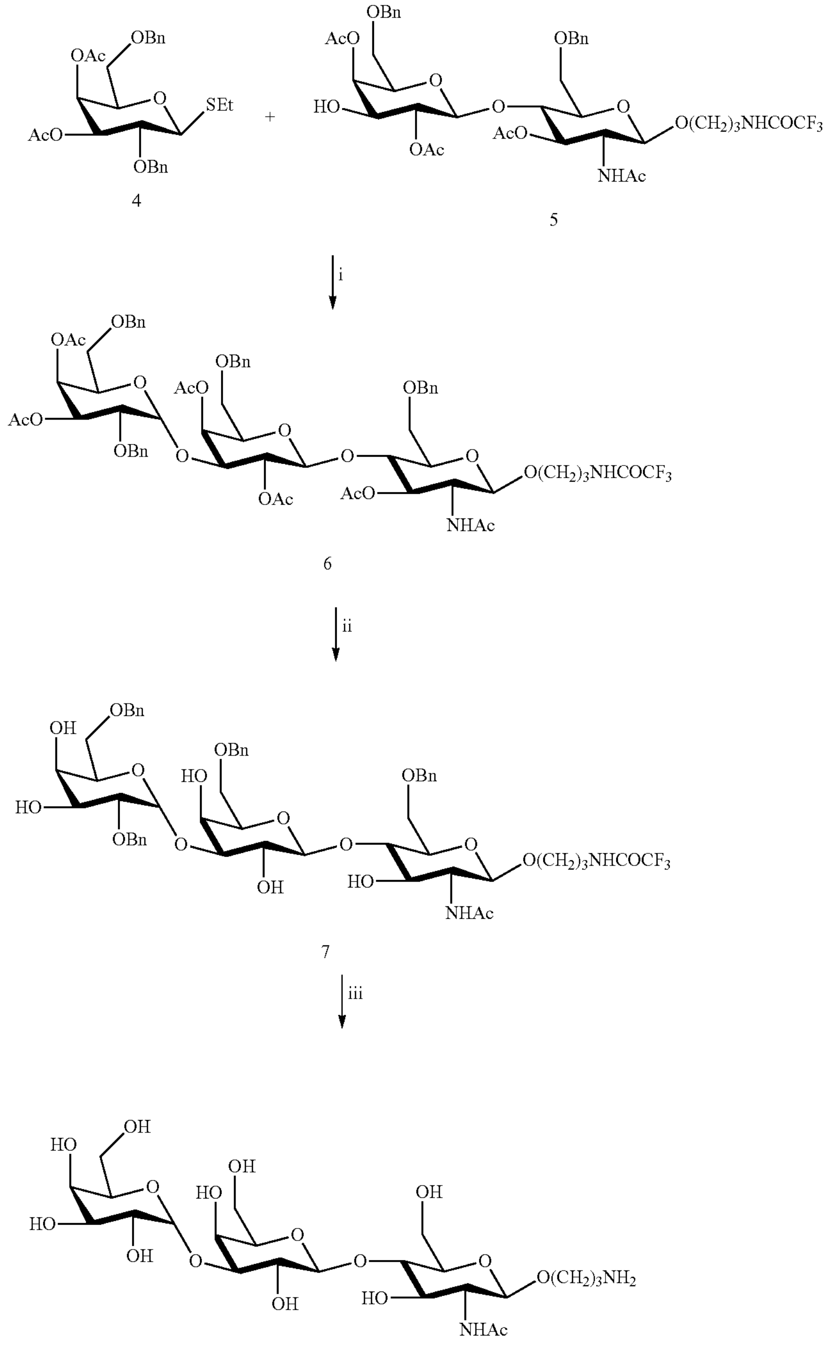

$^1H$ NMR ($D_2O$, characteristic signals), δ, ppm: 1.94-1.98 (m, 2H, $CCH_2C$), 2.07 (s, 3H, $NHC(O)CH_3$), 3.11 (m, J 6.92, 2H, $NCH_2$), 4.54 and 4.56 (2d, 2H, $J_{1,2}$ 8.06, $J_{1,2}$ 7.87, H-$1^{I}$ and H-$1^{II}$), 5.16 (d, 1H, $J_{1,2}$ 3.87, H-$1^{III}$). $R_f$ 0.3 (EtOH-BuOH-Py-$H_2O$—AcOH; 100:10:10:10:3).

Preparation of (1R)-1-[17-[[O-α-D-galactopyranosyl-(1→3)—O-β-D-galactopyranosyl-(1→4)-2-(acetylamino)-2-deoxy-β-D-glucopyranosyl]oxy]-3-hydroxy-3-oxido-8,13-dioxo-2,4-dioxa-7,14-diaza-3-phosphaheptadec-1-yl]-1,2-ethanediyl ester of (9Z,9'Z)-9-octadecenoic acid (CAS RN 1821461-84-0)(9)

To a solution of the product 8 (52 mg, 0.086 mmol) in dry DMF (2 mL) was added 15 μL of $Et_3N$ followed by a solution of the product 3 (100.6 mg, 1.00 mmol) in $CH_2Cl_2$ (2 mL). The reaction was stirred for 2 hours at room temperature followed by sequential column chromatography (the first on Sephadex LH-20, and the second on silica gel eluting with $CH_2Cl_2$-EtOH-$H_2O$; 6:5:1) to afford the product 9 (105.6 mg, 84%). $R_f$ 0.5 ($CH_2Cl_2$-EtOH-$H_2O$; 6:5:1)

SCHEME III

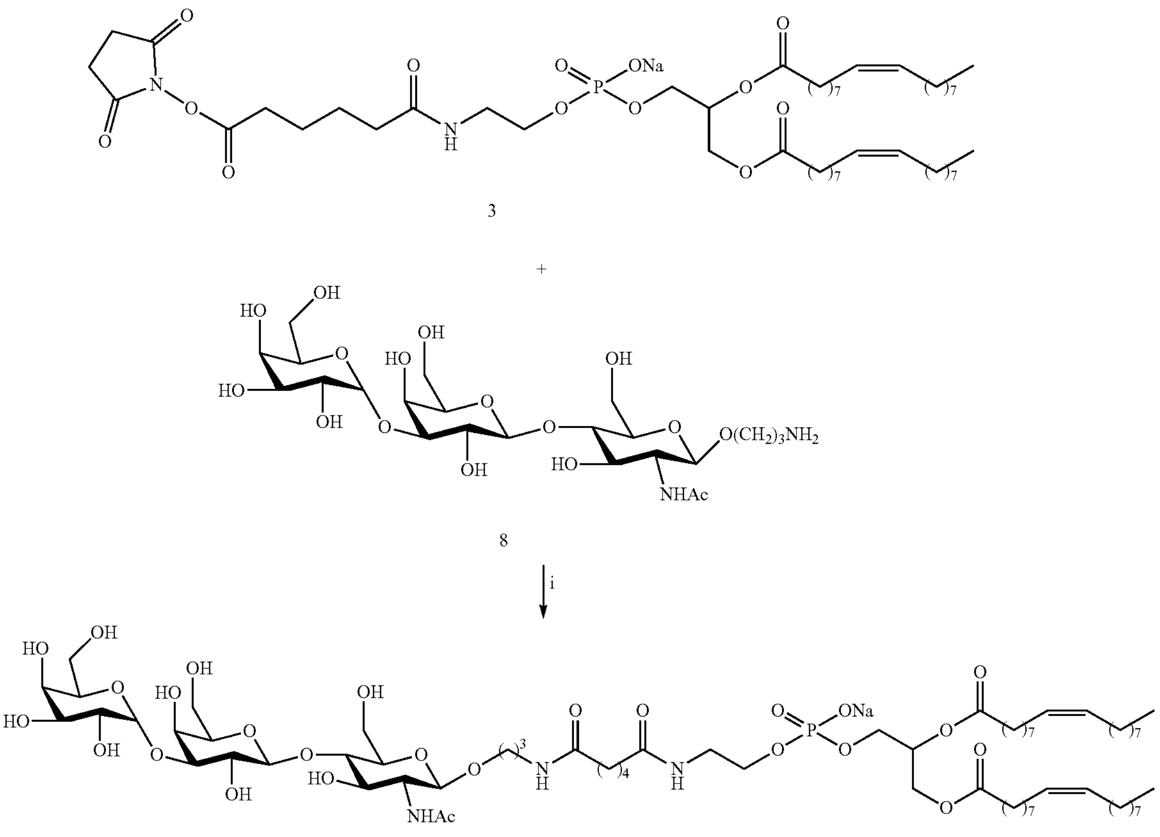

3

+

8

9

$^1H$ NMR (700 MHz, $CDCl_3$-$CD_3OD$ 1:1, 30° C.), δ, ppm, selected: 5.45-5.54 (m, 4H, 2x-CH═CH—), 5.34-5.43 (m, 1H, —$OCH_2$—CHO—$CH_2O$—), 5.18 (d, 1H, $J_{1,2}$ 2.52, H-$1^{III}$), 4.61 (d, 1H, $J_{1,2}$ 7.57, H-$1^{II}$), 4.60 (dd, 1H, J 2.87, J 12.00, C(O)OCHHCHOC$H_2$O—), 4.56 (d, 1H, $J_{1,2}$ 8.39, H-$1^{I}$), 4.36 (dd, 1H, J 6.8, J 12.00, —C(O)OCHHCHOC$H_2$O—), 4.19 (d, 1H, $J_{3,4}$ 2.48, H-$4^{II}$), 4.13-4.18 (m, 2H, —CHO—$CH_2$OP—), 3.52-3.62(m, 3H, PO—$CH_2$—C$H_2$—NH, —$CH_2$—CHH—NH), 3.29-3.35 (m, 1H, —$CH_2$—CHH—NH), 2.45-2.52 (m, 4H, 2x-$CH_2$—CO), 2.36-2.45 (m, 4H, 2x-$CH_2$—CO), 2.14-2.22 (m, 11H, 2x(—$CH_2$—CH═CH—$CH_2$—), NHC(O)$CH_3$), 1.85-1.96 (m, 2H, O—$CH_2CH_2CH_2$—NH), 1.73-1.84 (m, 8H, $COCH_2CH_2CH_2CH_2CO$ and 2x($COCH_2CH_2$—), 1.36-1.55 (m, 40H, 20 $CH_2$), 1.05 (t, 6H, J 6.98, 2 $CH_3$).

C70H126N3026P; MALDI MS: m/z 1480 (M Na+H); 1496 (MK+H); 1502 (MNa+Na), 1518 (M Na+K)

Rabbit Studies

Administration of the Antigen-Lipid Construct

Blood was collected from the saphenous vein of two rabbits (rabbit #1; rabbit #2) prior to administration of the antigen-lipid construct. The antibody titre of the blood collected from each rabbit was measured using hRBCs. Prior to the infusion a volume of blood equal to the volume of dispersion to be infused was withdrawn from the subclavian vein. The antigen-lipid construct was administered to each rabbit as a 20 mg/ml dispersion in saline by intravenous infusion into the subclavian vein. The antigen-lipid construct was administered at a rate of 10 mg per 100 g bodyweight of the rabbit. The rabbits were monitored post-infusion and observed for adverse reaction to the administration of the antigen-lipid construct. No adverse reactions were observed.

Determination of In Vivo Modification of rRBCs

Blood was collected from the saphenous vein of each rabbit one day following the administration of the antigen-lipid construct and the rRBCs separated from the serum. The separated rRBCs were washed three times and assessed for antigen expression using the DIAMED™ card platform. 30 μl of a 1.6% (pcv) rRBC suspension and 30 μl of anti-A monoclonal antibody were mixed and the cards spun and read. Rabbit #1 had a nil anti-A titre and rabbit #2 had a titre of 1:16 prior to infusion as measured against type A hRBCs. The rRBC agglutination scores as measured in the DIAMED™ card platform are presented in Table 1.

TABLE 1

Comparison of agglutination scores for rRBC pre-infusion, rRBC from rabbit infused with antigen-lipid construct (post infusion), rRBC modified in vitro by contacting with antigen-lipid construct and A hRBC.

| | | rRBC pre-infusion | rRBC post-infusion | modified rRBC* | A hRBC |
|---|---|---|---|---|---|
| Pre-immunisation serum | IgM | 0 | 0 | 0 | 0 |
| | IgG | 0 | 0 | 0 | 0 |
| Post-immunization/pre-infusion serum | IgM | 0 | 4+ | 4+ | 4+ |
| | IgG | 0 | 4+ | 4+ | 4+ |

TABLE 1-continued

Comparison of agglutination scores for rRBC pre-infusion, rRBC from rabbit infused with antigen-lipid construct (post infusion), rRBC modified in vitro by contacting with antigen-lipid construct and A hRBC.

| | | rRBC pre-infusion | rRBC post-infusion | modified rRBC* | A hRBC |
|---|---|---|---|---|---|
| Monoclonal anti-A | IgM | 0 | 4+ | 4+ | 4+ |

Intravenous administration of the antigen-lipid construct at a rate of 10 mg per 100 g bodyweight is effective to change the level of antigen expressed at the surface of circulating rRBCs with no observable consequences on the health of the subject rabbit.

Modification of the Titre of Reactive IgM Antibody in Plasma

Prior to immunisation a sample of blood was taken from the marginal ear vein of a rabbit. Indicator cells were prepared by contacting the rRBCs with a dispersion of the antigen-lipid construct at a concentration of 2 mg/ml. A rabbit (id #250) was immunized by subcutaneous injection of blood group A saliva mixed with Titremax™ adjuvant. Two weeks after immunization a sample of blood was taken from the marginal ear vein of the rabbit. The antibody titre of the serum of the blood obtained from the rabbit pre- and post-immunization was determined. Three weeks after immunization 2 ml of a dispersion of the antigen-lipid construct at a concentration of 25 mg/ml was infused into the marginal ear vein of the rabbit and the subject monitored for any signs of an adverse reaction for 4 hours. At 2 hours and 24 hours post-infusion a sample of blood was collected from the marginal ear vein of the rabbit and the serum separated. Serial dilutions of the serum collected prior to infusion with the antigen-lipid construct 2 hours post-infusion and 24 hours post-infusion were prepared. The antibody titre was determined by mixing 30 μl of each dilution and 30 μl of a 5% (pcv) suspension of rRBC modified with the antigen-lipid construct. The agglutination score for each mixture was read by tube serology. The titre of antibodies determined for the dilutions of sera are presented in Table 2.

TABLE 2

Titres of anti-A IgM in rabbit serum pre- and post-infusion measured by agglutination with rRBC cells modified in vitro by contacting with the antigen-lipid construct.

| | Serum dilution | | | | |
|---|---|---|---|---|---|
| | 1:2 | 1:4 | 1:8 | 1:16 | 1:32 |
| Pre-immunisation | 0 | 0 | 0 | 0 | 0 |
| Post-immunisation & pre infusion | 4+ | 3+ | 2+ | w | 0 |
| 2 hours post infusion | 0 | 0 | 0 | 0 | 0 |
| 24 hours post infusion | 3+ | w | 0 | 0 | 0 |
| Anti-A control | 4+ | 4+ | 3+ | 2+ | w |

Normal behaviour of the subject rabbit was observed within 10 minutes of the infusion of the antigen-lipid construct and no adverse reactions were observed. The antigen-lipid construct was able to be infused into the subject rabbit post-immunization with no observable adverse reaction. A reduction in the measurable titre of circulating antibody is observed at 2 hours following intravenous infusion with the antigen-lipid construct and a partial reduction in the titre was observed 24 hours following intravenous indicating a transient neutralisation of circulating antibody (IgM).

Modification of the Titre of Reactive IgG and IgM Antibody in Plasma

Modified rRBC (indicator cells) and an immunized rabbit were prepared as described above. Four weeks following immunization a sample of blood was taken from the saphenous vein of the rabbit and the rRBC and serum separated. The antibody titre of the serum was determined. Five weeks following immunization a volume of blood equal to the volume of the dispersion of the antigen-lipid construct to be infused was withdrawn from the subclavian vein of the subject rabbit. A dispersion of the antigen-lipid construct at a concentration of 20 mg/ml in saline was administered by intravenous infusion into the subclavian vein within circa 5 minutes. The antigen-lipid construct was administered at a rate of 10 mg per 100 g bodyweight. The subject rabbit was monitored for any adverse reaction to the infusion for 4 hours. Samples of blood were taken from the saphenous vein of the subject rabbit 5 minutes, 20 hours, and 48 hours following the infusion and the rRBC separated from the serum. The rRBCs were washed 3 times. Serial dilutions of the serum collected 5 minutes, 20 hours and 48 hours following infusion were prepared and the titre of antibody determined. For each dilution 30 μl was incubated with 30 μl of a 5% (pcv) of indicator cells and incubated as a suspension for 15 minutes as room temperature (RT). Each mixture was then centrifuged and the degree of agglutination determined. The samples were then re-suspended and incubated for a further 60 minutes at 37° C. and examined for agglutination and haemolysis. The samples were then washed 3 times in PBS and incubated with 30 μl anti-rabbit IgG antibody, centrifuged and examined for the presence of anti-A IgG. The lowest serum dilution providing a serology reading with the indicator cells of greater than 1+ are presented in Table 3. The agglutination scores of rRBC of the samples of blood obtained from the rabbit prior to and following infusion with the antigen-lipid construct are provided in Table 4.

TABLE 3

In vivo neutralization of circulating anti-A IgM and anti-A IgG antibodies

| | 5 minutes pre-infusion | 5 minutes post-infusion | 20 hours post-infusion | 48 hours post-infusion |
|---|---|---|---|---|
| IgM anti-A RT | 1:8 | 0 | 0 | 0 |
| IgM anti-A 37° C. | 1:4 | 0 | 1:2 | 1:2 |
| IgG anti-A | 1:16 | 1:4 | 1:4 | 1:8 |

Referring to Table 3 an infusion of the antigen-lipid construct appeared to neutralize the circulating anti-A antibody and the serum remained at least partially neutralized for 48 hours after infusion. The initial room temperature (RT) reactive anti-A IgM titre of 1:8 was completely neutralised and remained at this level 48 hours post infusion. The initial reactive anti-A IgG titre of 1:16 was neutralised to 1:4 for 20 hours, then increased to 1:8 after 48 hours indicating a transient neutralization of the circulating antibody. Referring to Table 4 rRBC's collected 5 minutes and 20 hours post an intravenous infusion of FSL A (10 mg/100 g body weight) were successfully transformed to express the A antigen. At 48 hours post infusion the synthetic molecules were not detected on the RBC membrane.

TABLE 4

| In vivo modification of rRBC by infusion of antigen-lipid construct. | | | |
|---|---|---|---|
| 5 minutes pre-infusion | 5 minutes post-infusion | 20 hours post-infusion | 48 hours post-infusion |
| 0 | 4+ | 3+ | 0 |

In vivo modification of rRBC to express a serologically detectable level of A antigen is observed following intravenous infusion of the antigen-lipid construct. The modification is concomitant with a reduction in the titre of circulating anti-A antibody of both the IgG and IgM classes. No adverse effects on the health of the subject rabbit are observed.

Rat Studies

Standard Immunisation Method

Rats were immunised in a one-step procedure according to protocols published for TiterMax® adjuvant. The rat was placed on its feet and was injected intramuscularly behind each hind quadricep with a 25 gauge needle. The following preparations were injected:

1. A 100 μl mixture of TiterMax® and natural glycolipid or synthetic antigen-lipid construct; or
2. Cells incorporating synthetic antigen-lipid constructs.

The rat was restrained on a towel on top of a table in a 25° C. room. It is well established that laboratory rats tolerate TiterMax® adjuvant well without the common injection site reactions that result from the Fruends adjuvant (Bennet 1992).

Blood Sampling to Assess Antibody Titres

The rat was anesthetized using the standard mixture of [8.75 mg Ketamine: 1.25 mg xylazine] per 100 g of rat body weight administered via the intraperitoneal (IP) route on a table in a 25° C. room. The rat was placed in a dorsal recumbency on a clean towel above the heating pad and a heating lamp positioned above the rat to prevent hypothermia during anesthesia. Pedal reflex test was then administered to test for complete state of anesthesia. The rat tail was immersed in warm water for 5-10 seconds to dilate the lateral tail vein. The site of needle insertion is prepared with a swab of 70% alcohol. Less than 0.5 ml of blood was drawn per sampling, which was less than 10% of total circulating blood volume recommended. A 25 gauge needle and 1 ml syringe was used for blood sampling.

Blood Sampling for RBC Serology

The rat was restrained by placing it in a restraint tube with its tail exposed. A small nick or needle prick was made on the distal end of the rat's tail and one drop of blood was collected using a heparinised capillary tube. Pressure was applied to the insertion site to stop bleeding. This blood was then washed and stored at 4° C. for up to 1 month for serology testing.

Infusions of Synthetic Antigen-Lipid Construct Solution

Two standard methods were used. The rat was anesthetized using the method described for blood sampling. 0.5 ml of synthetic antigen-lipid construct per 100 g of rat body weight was slowly infused over a period of 2-5 minutes into either the:

The lateral tail vein using the same technique as described in the blood sampling procedure; or The submandibular vein.

The submandibular vein method was used if blood was unable to be obtained from the lateral tail vein. A small 1 to 1.5 cm skin incision was made over the ventral neck area, slightly right of the center. The right submandibular vein was clearly visualised as it passed under the jaw bone. A small portion of the vein, approximately 5 mm section was carefully freed from all underlying tissue by using forceps. A small 25 gauge needle was carefully inserted into the isolated portion of the vein and 0.5 ml of synthetic antigen-lipid construct solution was infused slowly over 3-5 minutes. After the infusion, the incision site was closed with surgical suture or wound clips. The animals were closely monitored post-infusion for the first hour, then hourly afterwards.

Euthanasia

The animal was placed in a carbon dioxide partially filled chamber and sealed in for 10 minutes to ensure asphyxiation. Neck dislocation was then performed to complete the euthanasia process. All general animal manipulation and housing were within purpose built animal facilities providing a controlled environment for ventilation, temperature and light. The temperature is maintained by a thermostatically controlled air-conditioning and heating unit to obtain a desired ambient temperature of 21 to 23° C. A time-controlled light provides 12 hour light/dark cycles.

Mice Studies

A murine model of intravascular hemolytic transfusion reaction has been developed and used to demonstrate the principle of neutralization of circulating antibody by infusion of synthetic antigen-lipid constructs.

Preparation of Modified Murine Red Blood Cells (Murine a Kodecytes)

An amount of $A_{tri}$-$S_1$—$S_2$-DOPE (I) was diluted in sterile saline to provide a solution of $A_{tri}$-$S_1$—$S_2$-DOPE (I) at a concentration of 1 mg/mL. Mice red blood cells (RBCs) were washed 3 times in phosphate buffered saline (PBS) by centrifugation at 2700 rpm for 3 minutes. Equal volumes of the solution of $A_{tri}$-$S_1$—$S_2$-DOPE (I) and washed, packed mRBCs were mixed and incubated in glass tubes at 37° C. for 120 minutes with gentle agitation. Control cells were prepared by mixing equal volumes of packed human A RBCs and PBS, or packed naïve mice RBCs and PBS. Following incubation cells for infusion were washed three times in PBS and resuspended in SAG-M at a concentration (v/v) of 40:60 or 60:40. The transformation of mRBCs by $A_{tri}$-$S_1$—$S_2$-DOPE (I) (murine A kodecytes) was confirmed by agglutination using monoclonal anti-A reagent. Briefly, 30 μL of a 5% suspension of RBCs in PBS was incubated with 30 μL of monoclonal anti-A reagent at room temperature for 5 minutes. The incubated cells were then centrifuged and read for agglutination. The same procedure was repeated for the control cells (human A RBCs and naïve mice RBCs).

Infusion with Murine a Kodecytes

Three control mice (ID #001, ID #002, ID #003) were infused with 40 μL of murine kodecytes with an agglutination score of 4+. The serum reactivity against murine A kodecytes was assessed post infusion. No serum reactivity was detected. The reactivity of serum with A glycolipids of RBCs was also negative (Table 5).

Elicitation of a Antibody Expression

C57/B6 black mice were administered concentrated saliva comprising A antigen (human A $Le^{a-b+}$ saliva) in combination with TITREMAX™ gold adjuvant to elicit production of anti-A antibodies. A volume of 100 μl of an emulsion of 1 part saliva to 1 part TITREMAX™ was injected subcutaneously behind the head or in the flank of an anesthetized mouse. An electronic identification tag was used to identify each mouse. The administration was repeated three times at three week intervals. The sera of mice (ID #4117, ID #4977) were assessed for reactivity against murine A kodecytes. The elicitation of reactivity was demonstrated by agglutination of the murine A kodecytes. The reactivity of the sera with A glycolipids of RBCs was also confirmed (Table 5). Three mice (ID #7698, ID #1144, ID #9499) were transfused with a 40 μl volume of murine A kodecytes in sterile saline via the subclavian vein. The sera of the mice were assessed for reactivity against murine A kodecytes and with A glycolipids of RBCs as above. Reactivity for each serum sample was confirmed in at least one assay. Levels of free hemoglobin in the serum or plasma for each mouse were assessed at 30 minutes following infusion with the murine A kodecytes. Free hemoglobin was observed (Table 5). Three mice (ID #4605, ID #5234, ID #8553) were transfused with a larger 60 μl volume of murine A kodecytes in sterile saline via the subclavian vein. Increased levels of free hemoglobin in the serum or plasma of each mouse were observed at 30 minutes following infusion. In addition hemoglobin was observed in the urine of each mouse (Table 5). Three mice (ID #4422, ID #3032, ID #6440) were infused with a 200 μl volume of a 20 mg/mL dispersion of $A_{tri}$-$S_1$—$S_2$-DOPE (I) in sterile saline via the subclavian vein (4 mg $A_{tri}$-$S_1$—$S_2$-DOPE (I) per mouse). No free hemoglobin was detectable in the serum or plasma of each mouse 30 minutes following infusion. No free hemoglobin was detectable in the urine. No reactivity of the sera of each mouse with A glycolipids of RBCs was observed. Notwithstanding these observations the in vivo transformation of murine RBCs (A antigen positive as determined by monoclonal anti-A antibody) was demonstrated 1 to 3 hours following infusion. The presence of in vivo transformed A kodecytes in the absence of serum reactivity appears to demonstrate the ability of infused $A_{tri}$-$S_1$—$S_2$-DOPE (I) to neutralize circulating anti-A antibody for at least a transient period. It is suggested that the administration of synthetic antigen-lipid constructs may therefore be employed to mitigate the risk of clinically significant transfusion reactions attributable to circulating antibody. At about 3 days post infusion the red blood cells had become A antigen negative and the mice survived the procedure with no observations of adverse effects.

Preparation of Modified Murine Red Blood Cells

Blood was collected from mice, centrifuged and the serum removed. The red blood cells (RBCs) were washed three times in PBS and pooled. Equal volumes of washed, packed RBCs and dispersions of F-S-L construct(s) in phosphate buffered saline (PBS) were mixed and incubated for two hours at 37° C. with gentle, intermittent mixing.

The modified RBCs were then washed three times in PBS and resuspended in a human red cell transfusion medium (sucrose, adenine, glucose, mannitol solution). Modification of the murine RBCs was confirmed by agglutination using:

1. monoclonal anti-A reagent for red blood cells modified with the F-S-L construct where F was the blood group A trisaccharide; and
2. monoclonal anti-B reagent for RBCs modified with the F-S-L construct where F was the blood group B trisaccharide.

Where the RBCs had been modified with F-S-L construct where F was biotin, modification was confirmed by fluorescence microscopy using Avidin-Alexafluor™ 488. Briefly, a volume of 2 μL Avidin-Alexafluor™ 488 that had a concentration of 0.1 mg/mL in PBS was added to a 2 μL volume of packed modified RBCs. The suspension was incubated for 20 minutes and then washed three times in the human red cell transfusion medium. In order to prevent clumping the final pellet of packed modified RBCs was incubated for 2 minutes at 37° C. in the presence of a 2 μL volume of biotin at a concentration of 1 mg/mL in PBS. The mixture was then centrifuged to remove excess biotin and the pellet of modified RBCs resuspended in the human red cell transfusion medium at a ratio of about 1:10 (v/v). The fluorescent signal (1.9 ms) was observed using a 40× objective (Olympus BX51 Fluorescence microscope).

Administration of Compatible and Incompatible Modified Red Blood Cells to Mice

Figure 2:
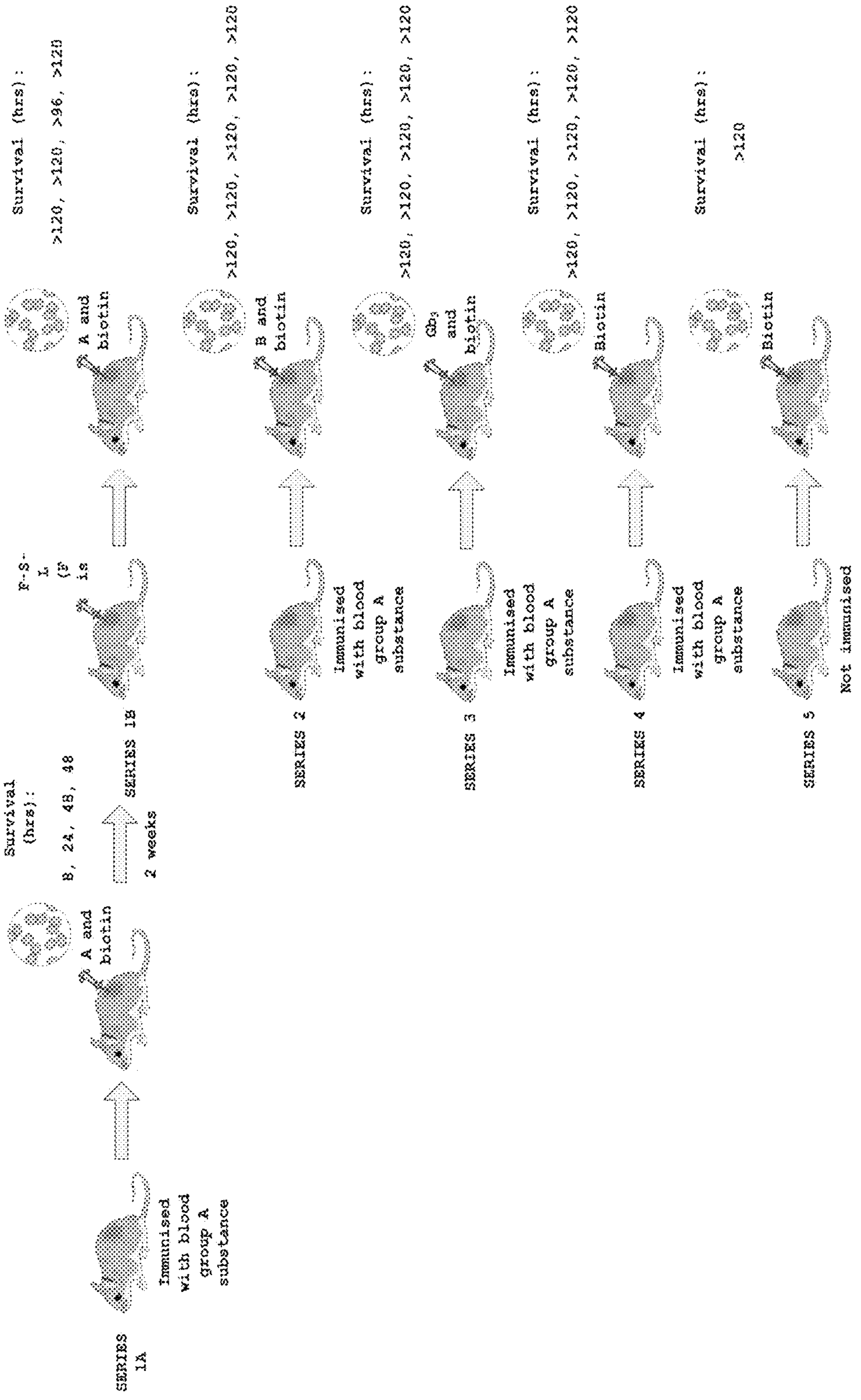
FIG. 2. Schematic representation of control and trial series described under the heading Administration of compatible and incompatible modified red blood cells to mice.

Mice immunized with blood group A substance were weighed and electronically tag checked and anaesthetized. A series of animals were immunized in parallel with the test and control series animals and their antibody status confirmed by thin layer chromatography. All immunized animals (n=4) were confirmed as anti-A positive against human blood group A RBCs and against F-S-L construct where F was the blood group A trisaccharide and blood group A type 2 glycolipid by solid phase analysis. The modified RBCs (F-S-L constructs where F was either the blood group A or B trisaccharide) administered to test animals provided a maximum 4+ reaction score with the corresponding anti-A or anti-B reagent. Either four or five immunized animals were used in each of the test and control series. A description of the test and control series is provided in Table 6 and illustrated schematically in FIG. 2.

A volume of 200 μL of a suspension of modified RBCs in the human red cell transfusion medium (20:180(v/v)) was injected into the subclavian vein of the test animal. The time of administration was noted and after three minutes a haematocrit tube blood collection was taken by a needle prick in the subclavian vein. A volume of about 50 μL of blood was collected from the test animal into anticoagulant in an eppendorf tube. For subsequent sampling of blood at time intervals of 2, 8, 24, 48, 72, 96 and 120 hours after administration the tails of the test animals where anaesthetised with EMLA cream for about 5 minutes. The tails were then warmed under a heat lamp for up to two minutes and blood obtained by tail vein incision. Collection of blood from each test animal was ceased when no fluorescence attributable to conjugation of Avidin-Alexofluor™ 488 to modified RBCs was detectable in 10 high power fields (circa $10^4$ RBCs). The post administration blood collection time (hours) at which fluorescence attributable to modified RBCs was no longer detectable is provided in Table 7.

Interpretation

The time of collection at which fluorescence attributable to modified RBCs was no longer detectable is taken to correspond to the survival time of the modified RBCs in the circulatory system of the test animal. Incompatible modified RBCs when administered to test animals without a prior infusion of the modifying F-S-L construct were indicated to have a survival time in the circulatory system of the test animal of no longer than 48 hours. Where an infusion of the modifying F-S-L construct was administered to the same test animals prior to administration of the corresponding modified RBCs the survival time of the administered RBCs was comparable with the survival time of the compatible modified RBCs. Compatible RBCs modified with F-S-L construct (s) where F was either the blood group B trisaccharide or biotin had a survival time in the circulatory system of the test animals of greater than 120 hours. The survival of these compatible modified RBCs in the circulatory system beyond 120 hours was not determined.

Although the invention has been described by way of exemplary embodiments it should be appreciated that variations and modifications may be made without departing from the scope of the invention. Furthermore, where known equivalents exist to specific features, such equivalents are incorporated as if specifically referred to in this specification.

TABLE 5

The absence of an entry means not determined.

| | 001 | 002 | 003 | 4117 | 4977 | 7698 | 1144 | 9499 | 4605 | 5234 | 8553 | 4422 | 3032 | 6440 |
|---|---|---|---|---|---|---|---|---|---|---|---|---|---|---|
| Elicitation of A antibody expression | x | x | x | ✓ | ✓ | ✓ | ✓ | ✓ | ✓ | ✓ | ✓ | ✓ | ✓ | ✓ |
| Volume of $A_{tri}$-$sp_1$-$sp_2$-DOPE (I) infused (μL) | 0 | 0 | 0 | 0 | 0 | 0 | 0 | 0 | 0 | 0 | 0 | 200 | 200 | 200 |
| Volume of murine A kodecytes infused (μL) | 40 | 40 | 40 | 0 | 0 | 40 | 40 | 40 | 60 | 60 | 60 | 0 | 0 | 0 |
| Reactivity of in vivo transformed A kodecytes | | | | | | | | | | | | ++++ | ++++ | ++++ |
| In vitro serum reactivity against murine A kodecytes | 0 | 0 | 0 | +++ | ++ | + | 0 | ++ | | | | | | |
| Free hemoglobin (plasma/sera) | | | | | | ++ | ++ | + | +++ | +++ | +++ | 0 | 0 | 0 |
| Free hemoglobin (urine) | | | | | | | | | ++++ | ++++ | Death | 0 | 0 | 0 |
| Reactivity of sera with RBC A glycolipids | −ve | −ve | −ve | +ve | +ve | +ve | +ve | +ve | | | | | −ve | −ve |
| Direct antiglobulin test (DAT) with anti-murine IgG | | | | | | | | | 0 | 0 | 0 | 0 | | |

TABLE 6

Control and trial series.

| | |
|---|---|
| Series 1a | Test series. 20 uL of murine kodecytes (modified with FSL-A and FSL-biotin) were infused into 4 mice each with anti-A. Blood was sampled at 2, 8, 24 and 48 hours and following staining with avidin-Alexafluor were observed for the presence of kodecytes in 10 high power fields (magnification 400X) under fluorescent microscopy |
| Series 1b | Test series. Two weeks later Series 1a mice were reused. 200 μL of FSL-A (20 mg/mL)was first infused as a solution followed by 20 μL of murine kodecytes (modified with FSL-A and FSL-biotin). Blood was sampled at 2, 8, 24, 48, 72, 96, and 120 hours and following staining with avidin-Alexafluor 488 were observed for the presence of kodecytes in 10 high power fields (magnification 400X) under fluorescent microscopy |
| Series 2 | Control series. 20 uL of murine kodecytes (modified with FSL-B and FSL-biotin) were infused into 5 mice, each with anti-A. Blood was sampled at 2, 8, 24, 48, 72, 96, and 120 hours and following staining with avidin-Alexafluor 488 were observed for the presence of kodecytes in 10 high power fields (magnification 400X) under fluorescent microscopy |
| Series 3 | Control series. 20 uL of murine kodecytes (modified with FSL-GB3 and FSL-biotin) were infused into 5 mice each with anti-A. Blood was sampled at 2, 8, 24, 48, 72, 96, and 120 hours and following staining with avidin-Alexafluor 488 were observed for the presence of kodecytes in 10 high power fields (magnification 400X) under fluorescent microscopy |
| Series 4 | Control series. 20 uL of murine kodecytes (modified only with FSL-biotin) were infused into 5 mice each with anti-A. Blood was sampled at 2, 8, 24, 48, 72, 96, and 120 hours and following staining with avidin-Alexafluor 488 were observed for the presence of kodecytes in 10 high power fields (magnification 400X) under fluorescent microscopy |
| Series 5 | Control series. 20 uL of murine kodecytes (modified only with FSL-biotin) were infused into 1 mouse without anti-A. Blood was sampled at 2, 8, 24, 48, 72, 96, and 120 hours and following staining with avidin-Alexafluor 488 were observed for the presence of kodecytes in 10 high power fields (magnification 400X) under fluorescent microscopy |

TABLE 7

| SERIES | Number of animals | Immunised with blood group A substance | 20 μL A + biotin modified RBCs | 20 μL B + biotin modified RBCs | 20 μL Gb3 + biotin modified RBCs | 20 μL Biotin (only) modified RBCs | Infusion with F-S-L (where F is blood group A trisaccharide (glycotope)) | Modified RBCs survival (hours) |
|---|---|---|---|---|---|---|---|---|
| 1a | 4 | + | + | − | − | − | − | 8, 24, 48, 48 |
| 1b | 4 | + | + | − | − | − | + | >120, >120, >96, >120 |

TABLE 7-continued

| SERIES | Number of animals | Immunised with blood group A substance | 20 μL A + biotin modified RBCs | 20 μL B + biotin modified RBCs | 20 μL Gb3 + biotin modified RBCs | 20 μL Biotin (only) modified RBCs | Infusion with F-S-L (where F is blood group A trisaccharide (glycotope)) | Modified RBCs survival (hours) |
|---|---|---|---|---|---|---|---|---|
| 2 | 5 | + | − | + | − | − | − | >120, >120, >120, >120, >120 |
| 3 | 5 | + | − | − | + | − | − | >120, >120, >120, >120, >120 |
| 4 | 5 | + | − | − | | − | | >120, >120, >120, >120, >120 |
| 5 | 1 | − | − | − | − | + | − | >120 |

REFERENCES

Bennett et al. (1992) *Journal of Immunological Methods,* 153, 31-40. Borman (2004) Chem. Eng. News, 82(32), 31-35. Chung et al. (2003) TRENDS in Immunology, 24 (number 6), 342-348. Galili (2004) Transplantation, 78 (number 8), 1093-1098. Henry et al, (1995) Vox Sang, 69 (number 3), 166-182. Hossaini (1972) American Journal of Clinical Pathology, 57, 489-493. Kannagi et al, (1982) Cancer Research, 42, 5249-5254. King and Monroe (2000) Immunological Reviews 2000, 176, 86-104. Ladsteiner et al. Levine (1978) Seminars Oncology, 5, 25-34. Mollison et al. (1972) Blood Transfusion in Clinical Medicine, Blackwell Scientific Publications. Monroe (2005) Transplantation, 79 (number 3), S12-S13. Pazynina et al (2002) Mendeleev Commun. 12(4), 143-145. Pazynina et al (2008) Russian Journal of Bioorganic Chemistry, Vol. 34, No. 5, 625-631. Wang et al (2005) Tetrahedron, 61, 4313-4321. Wardemann et al. (2004) J. Exp. Med., 200,191. Yang et al. (1998), J. Exp. Med., 187 (number 8), 1335-1342. Young and Moody (2006), Glycobiology, 16 (number 7), 103R-112R.

The invention claimed is:

1. A method of mitigating the risk of rejection of an allograft or xenograft in an incompatible recipient by neutralizing one or more populations of circulating antibody cross-reactive with a carbohydrate antigen expressed by the allograft or xenograft, comprising the step of administering to the recipient by intravenous infusion a concentration of a synthetic antigen lipid construct sufficient to neutralize the one or more populations of circulating antibody in the recipient, the construct having the structure F-$S_1$-$S_2$-L where F is the epitope of the carbohydrate antigen, $S_1$-$S_2$ is a spacer covalently linking F to L and selected to provide a construct that is dispersible in water and preferentially partitions into plasma relative to a naturally occurring glycolipid, and L is a di-acyl or di-alkyl glycerophospholipid.

2. The method of claim 1 where the neutralizing one or more populations of circulating antibody is for at least 20 hours from the administering to the recipient by intravenous infusion.

3. The method of claim 2 where the concentration of the synthetic antigen-lipid construct is at least 20 mg/mL.

4. The method of claim 3 where F comprises GalNAcα3(Fucα2)Galβ-, Galα3(Fucα2)Galβ-, GalNAcα3(Fucα2)Galβ-, Fucα2Galβ-, Galβ4GlcNAβ3(Galβ4GlcNAβ6)Galβ-, Galβ4GlcNAβ3-, Galβ4Glcβ-, GalβGlcNAcβ, Galβ3(Fucα4)GlcNAβ-, Fucα2Galβ3(Fucα4)GlcNAβ-, GalNAcα3(Fucα2)Galβ3(Fucα4)GlcNAβ-, Galα3(Fucα2)Galβ3(Fucα4)GlcNAβ-, Galβ4(Fucα3)GlcNAβ-, Fucα2Galβ4(Fucα3)GlcNAβ-, NeuAcα2-3Galβ3(Fucα4)GlcNAβ-, NeuAcα2-3Galβ4(Fucα3)GlcNAβ-, GalNAβ4(NeuAcα2-3)Galβ4-, GalβGalNAcα-, NeuAcα2-3Galβ4-, NeuAcα2-6Galβ4-, Galα4Galβ4-, GalNAcβGalα4Galβ4-, Galα4Galβ4GlcNAβ3-, Galβ3GalNAcβGalα4-, NeuAcα2-3Galβ3GalNAcβGalα4-, Galα3Galβ-, GalNAcα3GalNAcβGalα4- or GalNAcβGalNAcβGalα4-; $S_1$ is 2-aminoethyl, 3-aminopropyl, 4-aminobutyl, or 5-aminopentyl; $S_2$ is $-CO(CH_2)_2CO-$, $-CO(CH_2)_3CO-$, $-CO(CH_2)_4CO-$ or $-CO(CH_2)_5CO-$; and L is phosphatidylethanolamine.

5. The method of claim 4 where the construct has the structure:

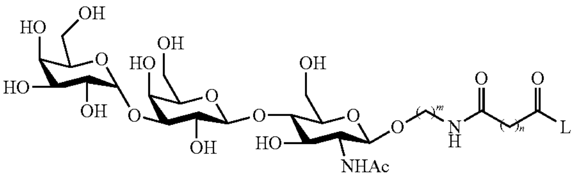

where m is the integer 2, 3, 4 or 5; n is the integer 2, 3, 4 or 5; and L is phosphatidylethanolamide.

6. The method of claim 5 where the construct has the structure:

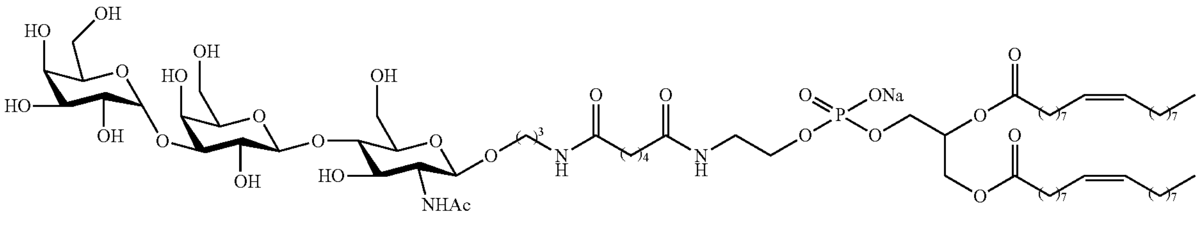

designated Galili-$S_1$-$S_2$-DOPE.

* * * * *